US011412982B2

(12) United States Patent
Parara et al.

(10) Patent No.: US 11,412,982 B2
(45) Date of Patent: Aug. 16, 2022

(54) WEARABLE CARE SECURITY SMART WATCH DEVICE

(71) Applicants: Andrew Parara, Hyde Park, MA (US); Selina Sekka, Milton, MA (US)

(72) Inventors: Andrew Parara, Hyde Park, MA (US); Selina Sekka, Milton, MA (US)

(*) Notice: Subject to any disclaimer, the term of this patent is extended or adjusted under 35 U.S.C. 154(b) by 346 days.

(21) Appl. No.: 16/507,106

(22) Filed: Jul. 10, 2019

(65) Prior Publication Data
US 2019/0328325 A1 Oct. 31, 2019

Related U.S. Application Data

(63) Continuation of application No. 15/162,121, filed on May 23, 2016, now abandoned.

(60) Provisional application No. 62/165,915, filed on May 23, 2015.

(51) Int. Cl.
A61B 5/00 (2006.01)
A61B 5/024 (2006.01)
A61B 5/11 (2006.01)
G04G 21/02 (2010.01)
G04G 21/04 (2013.01)
G16H 40/67 (2018.01)

(52) U.S. Cl.
CPC ............ A61B 5/681 (2013.01); A61B 5/0022 (2013.01); A61B 5/02438 (2013.01); A61B 5/1112 (2013.01); A61B 5/747 (2013.01); A61B 5/7445 (2013.01); G04G 21/025 (2013.01); G04G 21/04 (2013.01); G16H 40/67 (2018.01)

(58) Field of Classification Search
None
See application file for complete search history.

(56) References Cited

U.S. PATENT DOCUMENTS

| 6,618,328 | B1 * | 9/2003 | Ellner | G04B 19/30 368/278 |
| 2009/0082677 | A1 * | 3/2009 | Shih | A61B 5/02438 600/485 |
| 2013/0182915 | A1 * | 7/2013 | Hanna | G06F 21/32 382/116 |
| 2014/0278220 | A1 * | 9/2014 | Yuen | A61B 5/02427 702/150 |
| 2016/0147292 | A1 * | 5/2016 | Sunwoo | G06F 1/1677 713/323 |
| 2020/0218312 | A1 * | 7/2020 | Connor | G06F 3/1446 |

FOREIGN PATENT DOCUMENTS

CN 2927530 Y * 7/2007

* cited by examiner

Primary Examiner — Jay B Shah
(74) Attorney, Agent, or Firm — Bay State IP, LLC

(57) ABSTRACT

A wearable security device includes a strap and watch face base attached to the strap with a heart rate monitor on the backside of the watch face base that is placed on the vital signs of a user and records the vital signs of the user. Within the wearable security device is a memory for storage and at least one program configured to track and store the vital signs of the user. Also, an internal system is programmed to send a wireless alert signal in response to a vital sign of the user that indicates that the user is in danger.

10 Claims, 15 Drawing Sheets

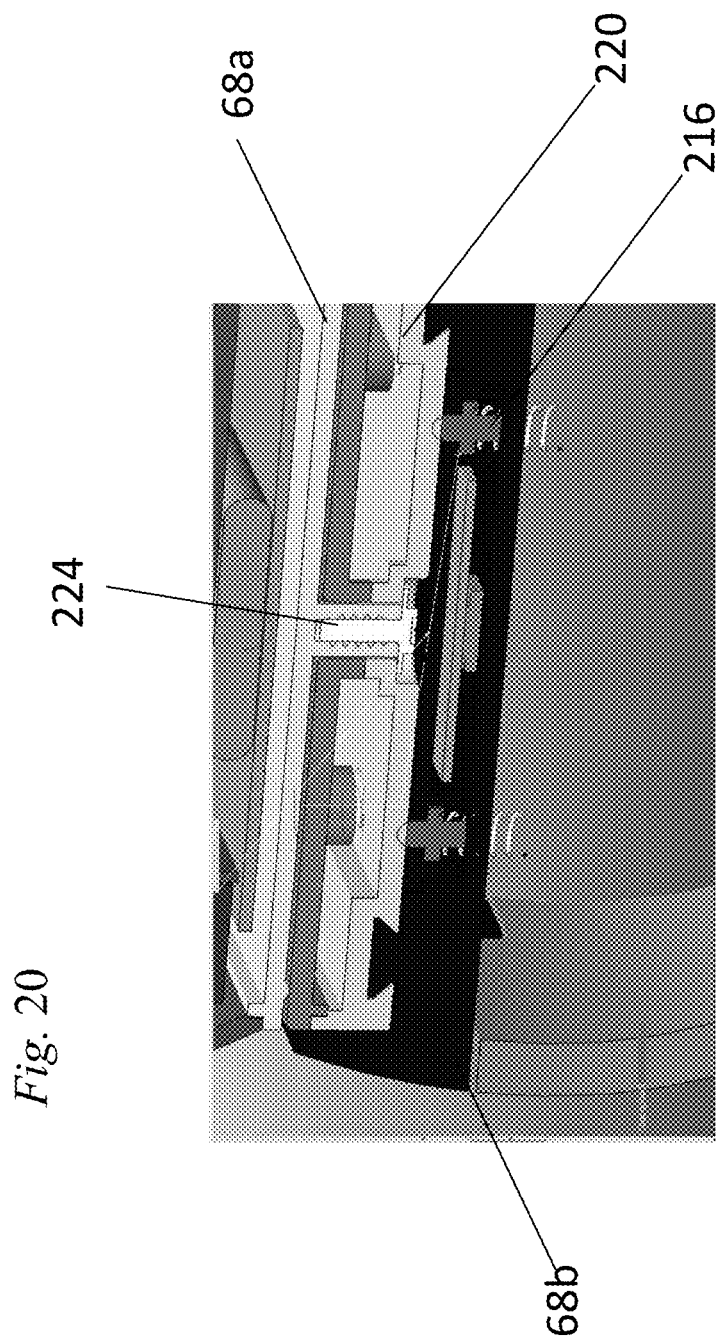

WEARABLE CARE SECURITY SMART WATCH DEVICE

CROSS REFERENCE TO RELATED APPLICATION

This application is a continuation application and claims priority to and takes the benefit of U.S. patent application Ser. No. 15/162,121 filed on May 23, 2016, which claims priority to and takes the benefit of U.S. Provisional Patent Application No. 62/165,915 filed on May 23, 2015, the contents of which are herein incorporated by reference.

FIELD OF INVENTION

The subject invention relates to a wearable device typically used to communicate, tell time, download applications for customization, such as voice recognition and act as an adaptable heart monitor alert to detect vital signs in an user's body to call for help if harmed or in need of medical assistance.

BACKGROUND OF THE INVENTION

The use of wired and wireless portable electronic devices continues to grow. Numerous portable user devices provide wireless connectivity. Wearable watches are used to tell time and recently have started to be used as a means of communication, synching with a user's cell phone. These watches are capable of numerous functions such as reviewing email, sending and receiving text messages, and even sending and receiving phone calls.

Other wearable devices exist to track a user's steps, sleep patterns, and count calories. These devices have helped users live a healthier lifestyle.

Other wearable devices are capable of transmitting personal assistance or emergency signals to friends, relatives, caregivers, and emergency personnel are also generally known. These devices usually require conscious activation of an emergency alert to notify responders of the existence of a medical, personal, or other emergency. These devices need the user to press a button or use some other deliberate signal activation by the user to notify for help. Traditionally, when someone is faced with a dangerous situation, whether it be witnessing a crime or being personally injured, he must dial a phone to ask for situations. In some instances, people are unable to vocalize the help they need because the circumstances do not allow them vocal communication.

SUMMARY OF THE INVENTION

The present invention, as illustrated herein, is clearly not anticipated, rendered obvious, or even present in any of the prior art mechanisms.

The present invention provides a wearable detecting device and in particular a sensing device where a user's heart rate is monitored to act as a personal body guard to protect a user against being robbed, hurt, and even kidnapped. The device would cut down on crime rates, prevent both children and adults from being harmed, and even be a potential lifesaver for users in dangerous circumstances. Individuals respond to fear in different ways. Some are unresponsive, frozen, or panicked. These human responses delay communicating for assistance either from the police, fire department, or ambulance services. These delays allow for criminals to get away, individuals to be further injured, or even for individuals to be held against their will.

In one embodiment, the wearable device is a watch phone that operates like a cell phone, but is worn around the wrist or arm. The watch has a transmitter strap that would lay flat against the vital signs of a user. The transmitter strap may read the user's vital signs to determine distress, adverse health conditions, and panic. The wearable device would act as a phone and may be programmed to notify the police, fire department, and ambulance services in the occurrence of a dangerous situation.

The transmitter strap may have a heart rate monitor that would be directly placed to a user's vital signs so that the user's pulse is monitored. The device may be programmed to learn the user's vital norms, averages, and patterns. Thus, the device will also be able to track vital abnormalities and further determine when a user is in distress based on vital signs.

In another embodiment, the wearable device, after notifying the police, fire department, and ambulance services that help is needed, is able to pinpoint the user's location with GPS services like lo jack, in order for emergency services to easily track where the help is needed.

In yet another embodiment, the wearable security device may platform a quad band frequency to fit the United States or other countries.

In yet another embodiment, the wearable security device may contain 4-8 GB of memory that allows a user to download applications for customizable security systems.

In another embodiment, the wearable device may have a screen with a 2-4 inch Thin Film Transistor ("TFT") touch screen, Bluetooth enables, android system with 2.0 mega pixel camera that works manually or voice controlled.

In yet another embodiment, the wearable security device may be multi-language compatible, powered by lithium batteries, and flash drive card or USB connection to transfer data between the wearable security device and a computer.

In another embodiment, the wearable security device may be voice controlled to turn the security system on or off depending on the user's situation.

In another embodiment, the wearable device provides a security system, which is easily attached to a user and easily managed.

BRIEF DESCRIPTION OF THE DRAWINGS

FIG. 20 illustrates an embodiment wherein the push pin mechanisms will hold the wearable care security smart watch device together in place and provide the necessary characteristics.

DETAILED DESCRIPTION OF SEVERAL EMBODIMENTS

Figure 1:
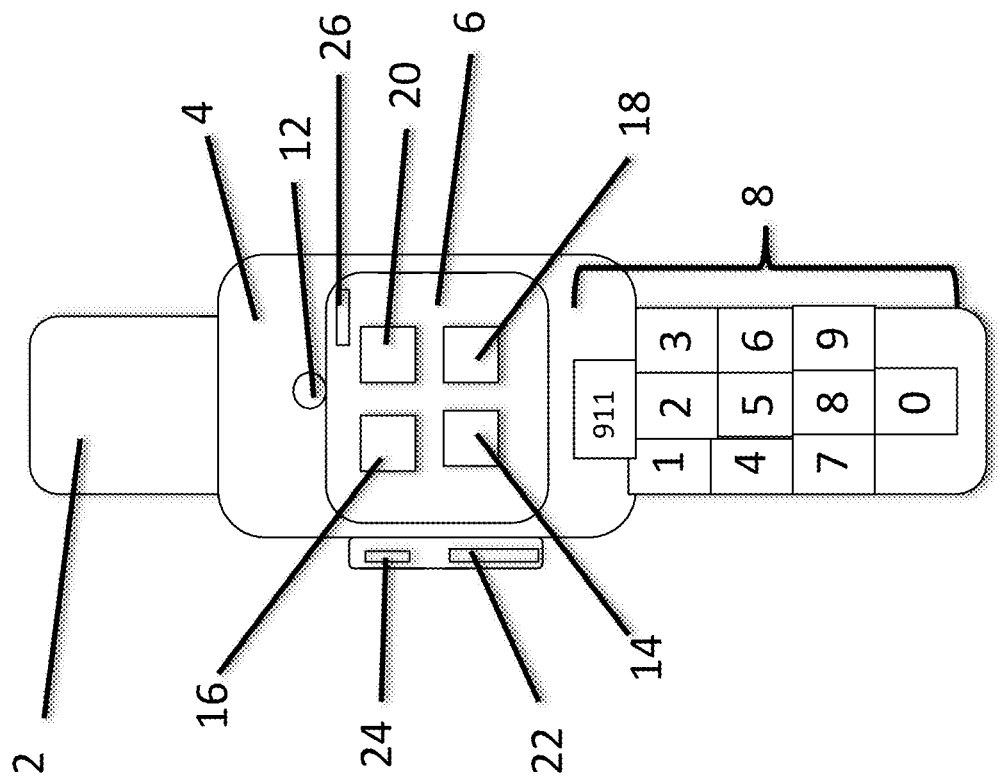
FIG. 1 illustrates one embodiment of the present invention wherein the wearable security device is a wearable care security smart watch device.

FIG. 1 illustrates one embodiment of the present invention which includes the overall structure of the wearable care security smart watch device 10. The wearable care security smart watch device has a strap 2 which can be worn around the user's wrist. The watch face base 4 would rest on the wrist so the bottom side of the watch face base would rest on the user's vital signals (See FIG. 3). On the strap there are sensitive touch dials 8 which are capable of being dialed like a phone.

The watch face base has a touch screen 6 which also displays a variety of options including, but not limited to, an ambulance contact option 16, a fire department contact option 15, a police department contact option 20, and a personal security system option 18 that would record and monitor the user's vital signs. Other customizable options may be available to the users where the user may decide to include other applications on the touch screen 6. The touch screen may also display the battery power 26 so the user knows when to recharge the wearable security device 10.

The wearable care security smart watch device 10 may also include a USB connection 22 in order for the user to attach the wearable security device to a computer or other device in order to allow the user to transfer data and provide extra storage. The wearable security device may also have a flash card 24 that is also capable of storing information. The wearable security device also may contain a 2.0 mega pixel camera 12 that works manually or through voice control.

Figure 2:
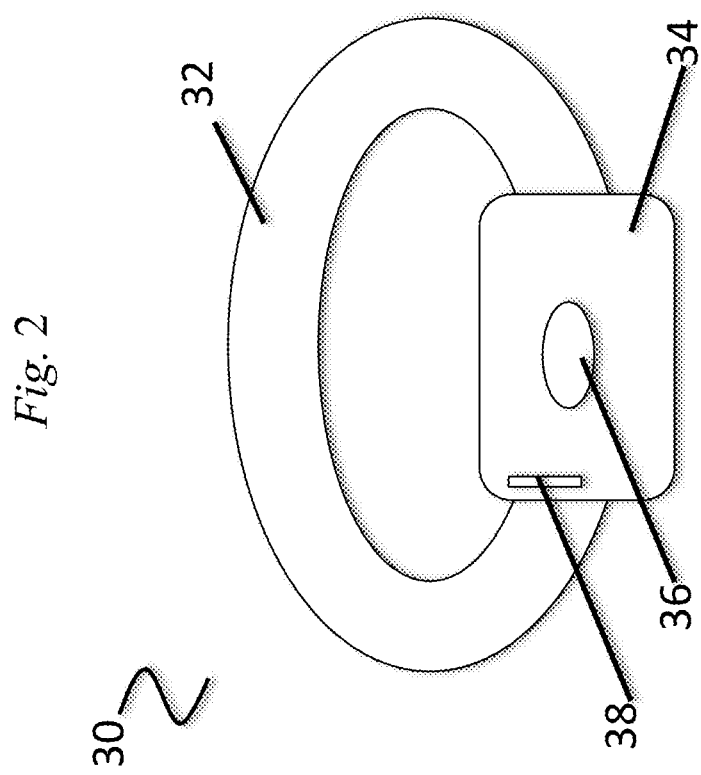
FIG. 2 illustrates another embodiment of the present invention wherein the wearable care security smart watch device also includes a transmitter strap that may be attached to the user's arm or chest.

FIG. 2 illustrates another embodiment of the current invention, which includes a transmitter strap 30. The transmitter strap may be attached to a user's chest and has a waterproof, elastic lining all around to protect the device from moisture and sweat 32. The transmitter strap is battery powered 38 and contains an electrode 36, on a plastic or metal backing plate 34, which reads the user's heart signal and sends the results to the wearable care security smart watch device.

Figure 3:
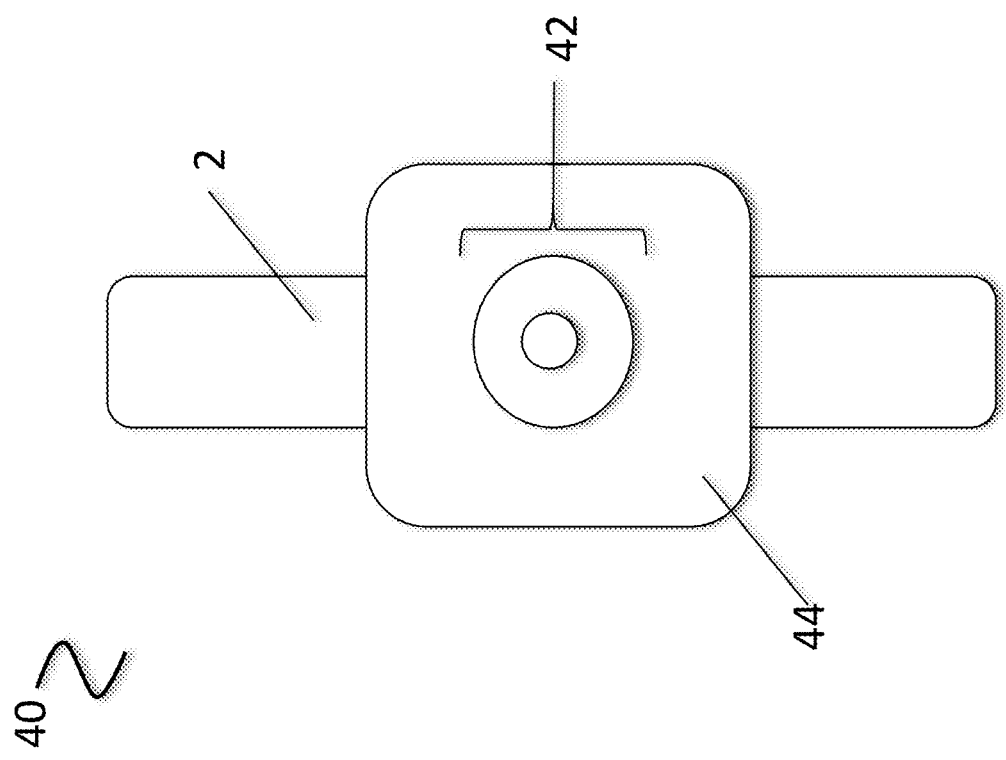
FIG. 3 illustrates the back side of the watch face displayed in FIG. 1.

FIG. 3 illustrates another embodiment of the present invention, specifically the backside of the watch face base of the wearable care security smart watch device 40. Attached to the strap 2 is a plastic or metal backing plate 44. Attached to the plastic or metal backing plate is an electrode heart rate monitor 42 that may be placed directly on the user's wrist and record and monitor the user's vital signs.

Figure 4:
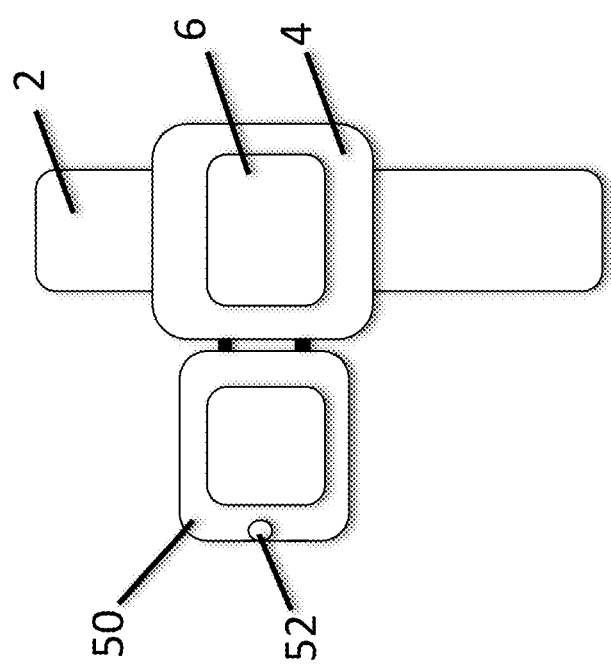
FIG. 4 illustrates another embodiment of the present invention which includes an adjustable watch face base.

FIG. 4 illustrates yet another embodiment of the present invention, which includes an adjustable touch screen. The touch screen may flip open to provide extra touch screen space for the user to download other applications. The flip-able screen 50 can be flipped up or adjusted to fit the needs of the user. Under the screen, there may be a 2.0 mega pixel camera 52 that is capable to snap shots at different desired angles.

Figure 5:
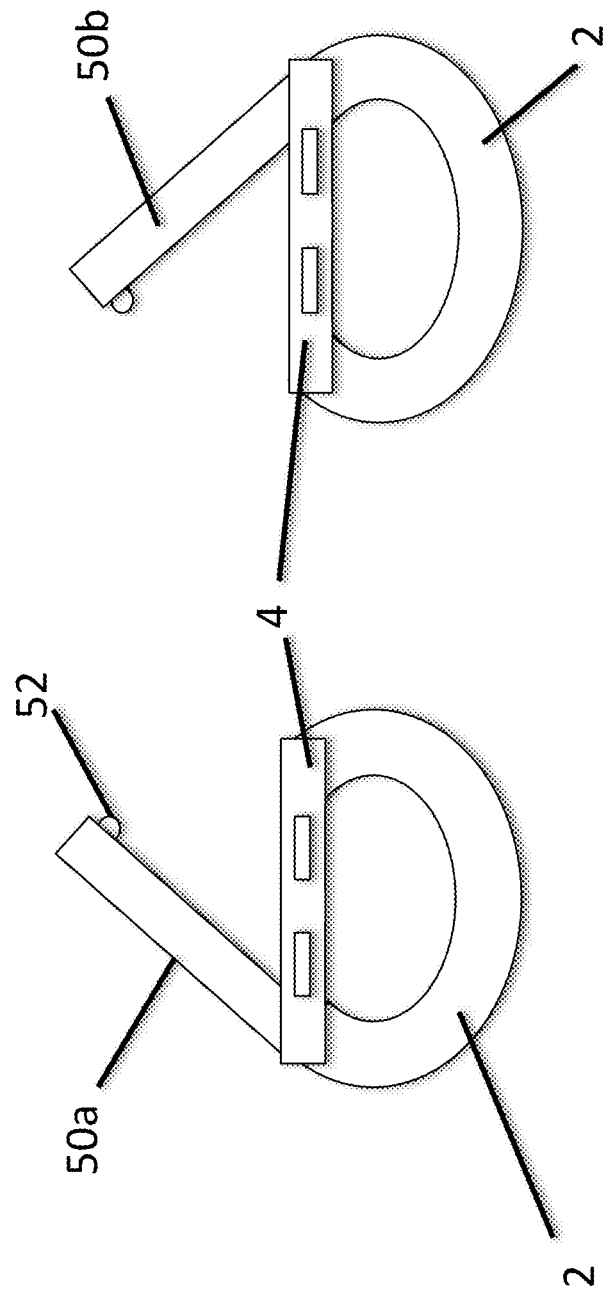
FIGS. 5a and 5b illustrates another embodiment of the present invention which includes an adjustable watch face base depending on the angle the user wants to use.

FIGS. 5*a* and 5*b* show different angles of the wearable care security smart watch device depending on the wrist the user chooses to wear the device. The flip-able screen may be adjusted to different angles for a better user view of the screen or for different angled pictures 50*a*, 50*b*. The back of the watch screen may also rotate 180 degrees for better screen viewing, self-picture taking, and other user-friendly functions. The back side of the watch face base is displayed in FIG. 3 which contains the heart rate monitor that is used to track and record the user's vital signs.

Figure 6:
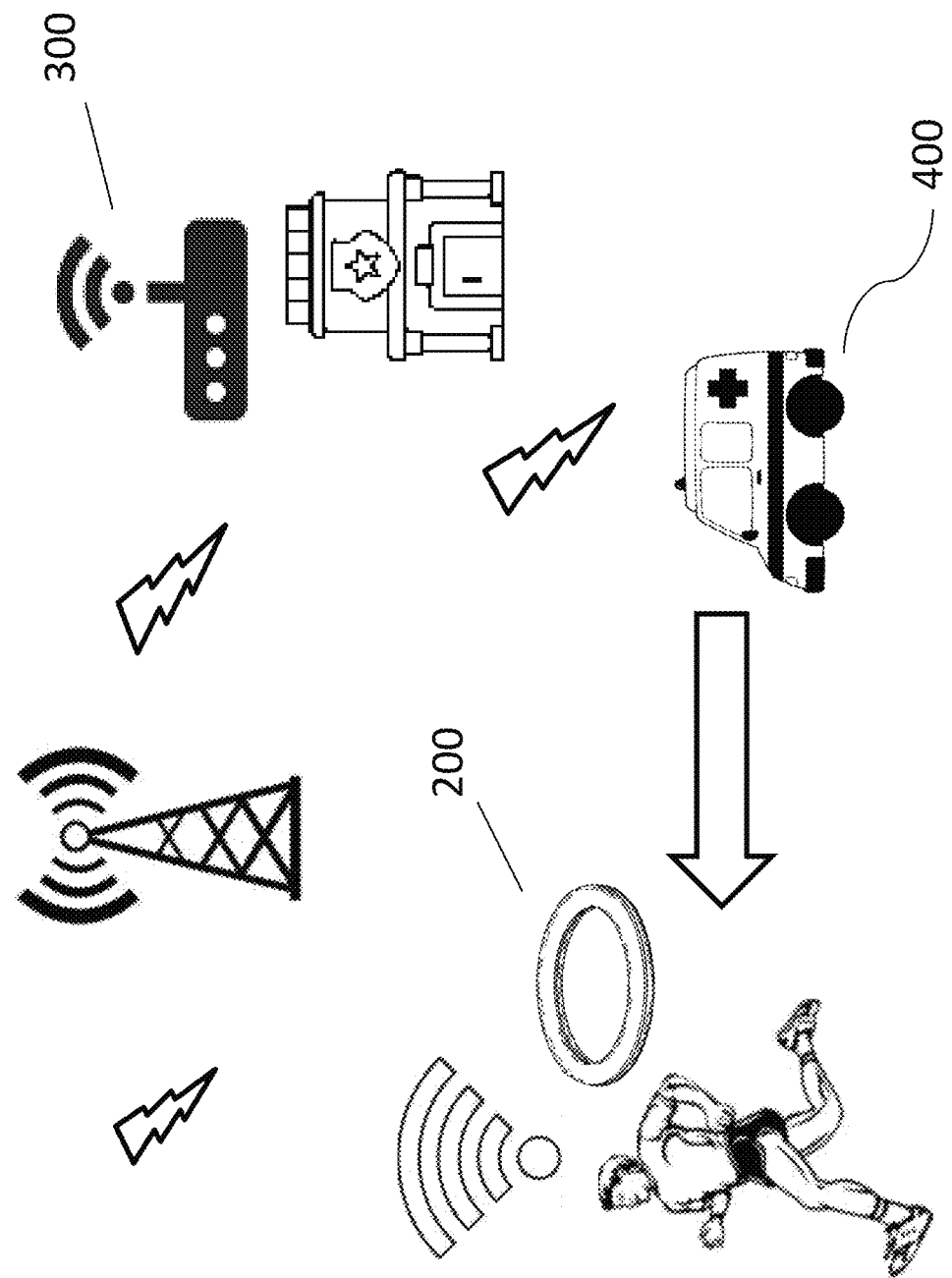
FIG. 6 illustrates the use of the wearable care security smart watch device and its interactions with third party emergency services.

FIG. 6 displays the entire system functioning with the wearable security device in action. In the present figure, the user is wearing the device 200. If the device records vital signs that indicate a dangerous or distressful situation, it signals a wireless system 300 which in turn would notify emergency authorities. The emergency authorities are then able to respond to the scene of distress 400 using GPS tracking to locate the user.

Figure 7:
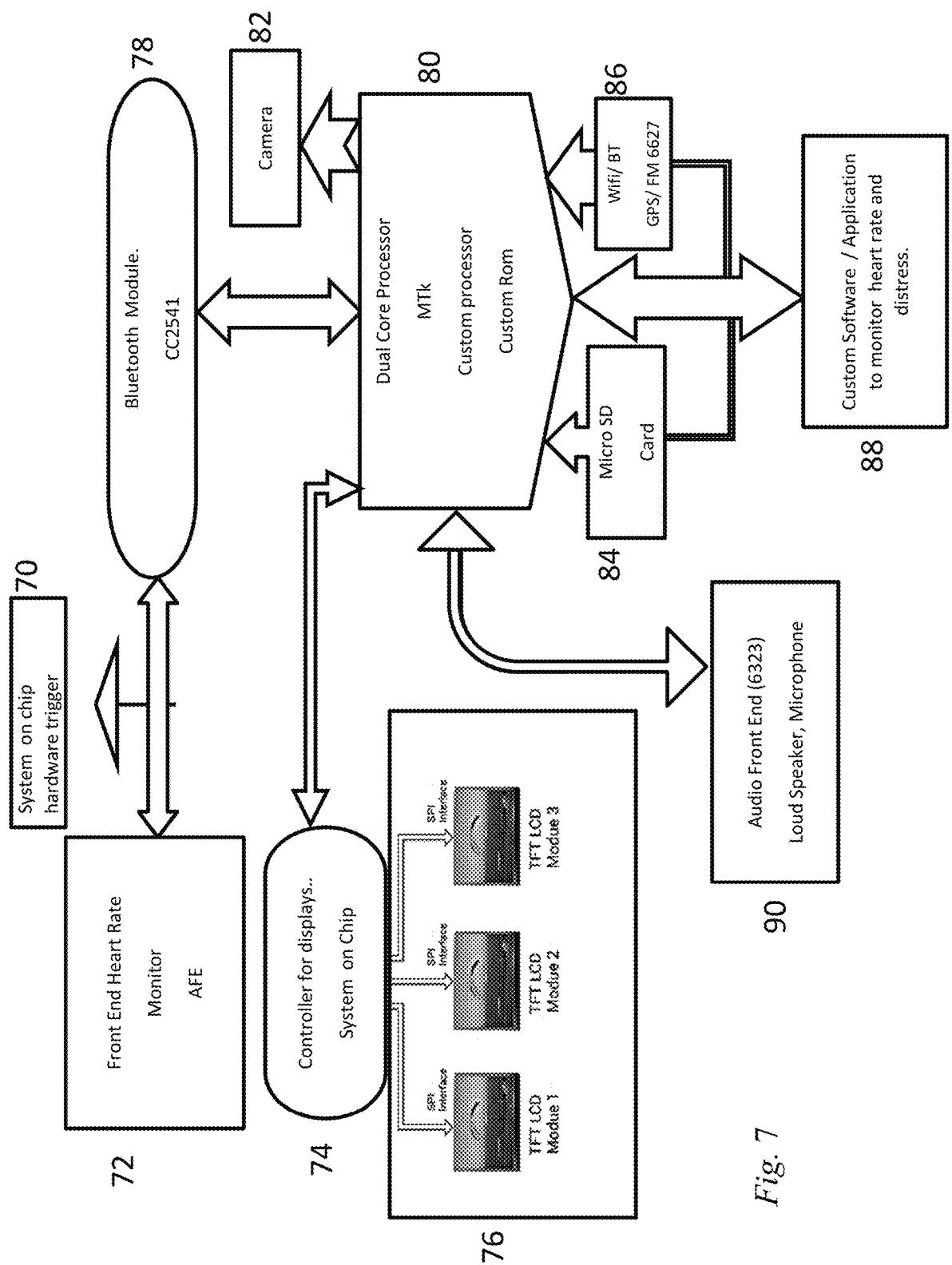
FIG. 7 illustrates is a flow diagram illustrating exemplary functions performed by the wearable care security smart watch device of FIG. 8.

FIG. 7 illustrates a flow diagram illustrating exemplary functions performed by the wearable care security smart watch device. In one embodiment, an audio front end (AFE) heart rate monitor or bio sensor 72 may connect to a main system on chip 74 through Serial Peripheral Interface 76 (SPI) or based on design Bluetooth module 78. Through a Bluetooth module 78, the wearable care security smart watch device may be able to transmit data to the main system on chip 74, the processor may be wireless due to the device being able to separate from the wrist band. A Bluetooth module is low energy consumption and may integrate with the heart rate monitor 72. A signal may be sent out via the Bluetooth module to the main system on chip being the processor 80 will give out all the information through SPI 76, SPI to programmatically handle the information, and is integrated into system on chip and hardware triggers 70 which will work with the heart rate monitor timing controller to where a code would be sent as a trigger, action trigger code will start alert and a countdown will start which will be controlled by the software/application 88.

In another embodiment, if the condition of the heart rate does not change, custom software/application 88 will have integrated voice integration which may ask the user of the wearable care security smart watch device a series of questions including but not limited to the user's status, health, issues, and/or concerns, etc. A user may also elect to use SMS messaging with vibration mode alerts. A user may also utilize a camera function 82 to capture surrounding area and issues.

In another embodiment, the custom software/application 88 may communicate with a storage device such as a micro SD internal storage device 84, or saved in a cloud computing platform. The wearable care security smart watch device will then be able to delineate the saved readings of the user for future reference.

An additional embodiment, if the stored reading are out of character or out of specification, a trigger will be sent to the processor and then a message will be transmitted to the software/application in Real Time of System. The system may also question the user and ask the user if he or she is okay or in distress 90. In one embodiment, if the user does not respond within a set time desired, the timing controller will send a trigger code through the processor from which will send the code signal to call emergency respondents. The software/application may then send the user's location through GPS location positioning 86 thus alerting the emergency respondents to the user's location.

In yet another embodiment, health information may be stored to the Micro SD, internal memory, or a cloud server 84. Information will be able to be obtained by medical respondents through USB pathway. Once a condition is determined, a device will set off emergency protocol and the device may lock. The user's name, health condition, and emergency contact number, along with other potential information will only be accessible by the emergency respondents and/or facilities.

Figure 8:
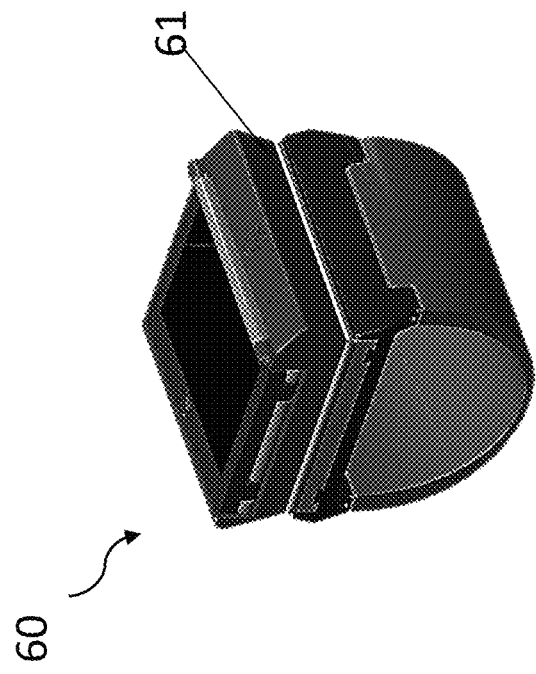
FIG. 8 illustrates another embodiment of the wearable care security smart watch device.

FIG. 8 illustrates another embodiment of the wearable care security smart watch device 60. Herein, the device is shown in complete form, completely assembled. As stated, the state of the art technology introduces new functionalities never utilized before by a watch device. Further, FIG. 8 illustrates the wearable care security smart watch device in a closed position 61.

Figure 9:
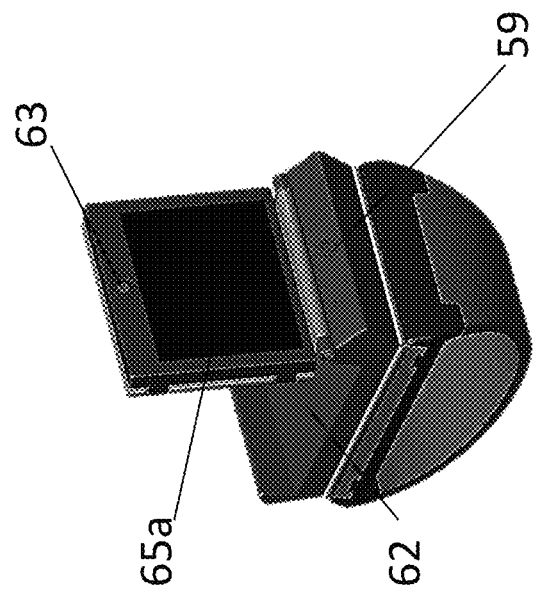
FIG. 9 illustrates yet another embodiment of the wearable care security smart watch device, wherein the screen of the wearable care security smart watch device is in an upright 90 degree angle.

FIG. 9 illustrates the wearable care security smart watch device, wherein the screen is adjusted to a 90 degree angle 62. As seen, on the front screen pictured is a front camera 63 that may be used to record, video call also known as V.O.I.P and take pictures. Also pictured is the front speaker 59 which may produce at least 75 decibels of volume. A microphone is located right next to the speaker.

Figure 11:
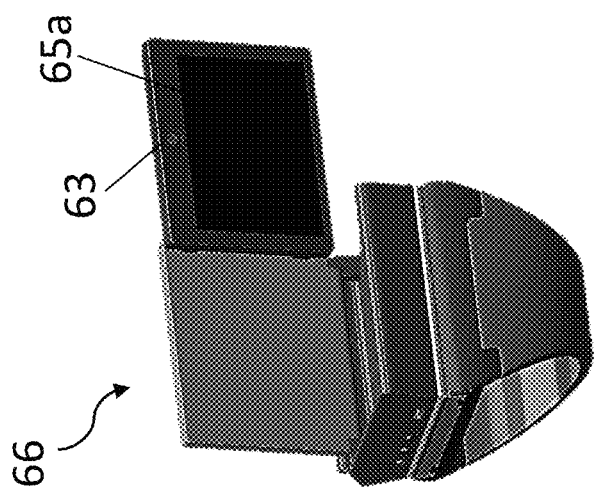
FIG. 11 illustrates yet another embodiment of the wearable care security smart watch device, portraying the screen at an additional angle.
Figure 10:
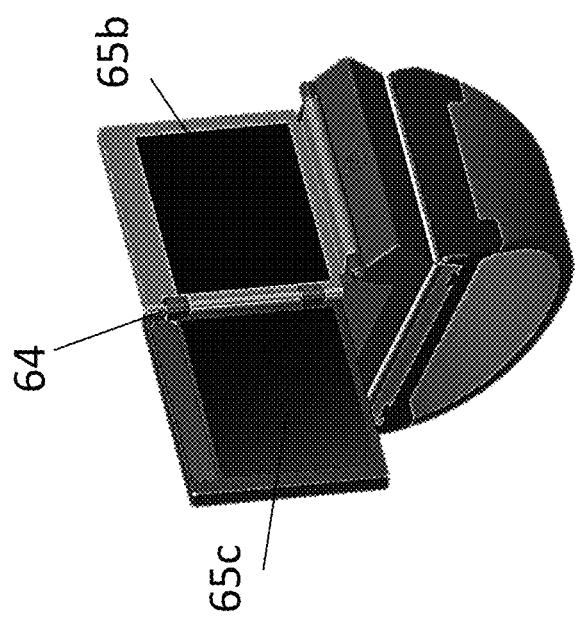
FIG. 10 illustrates another embodiment of the wearable care security smart watch device, wherein the screen display is in an open position.

FIG. 10 illustrates the screen of the wearable care security smart watch device, wherein the screen display is in an open position 64. When opened, there is a two screen display 65b and 65c. Further there may be multiple screens used with the wearable care security smart watch device. The purpose of having multiple screens is to achieve more space when needed and multitasking functions. In FIG. 11, the first screen 65a (also shown in FIG. 1) comprises a fixed camera 63 which will be able to take pictures, video record, and also but not limited to being able to achieve V.I.O.P. communications.

Figure 12:
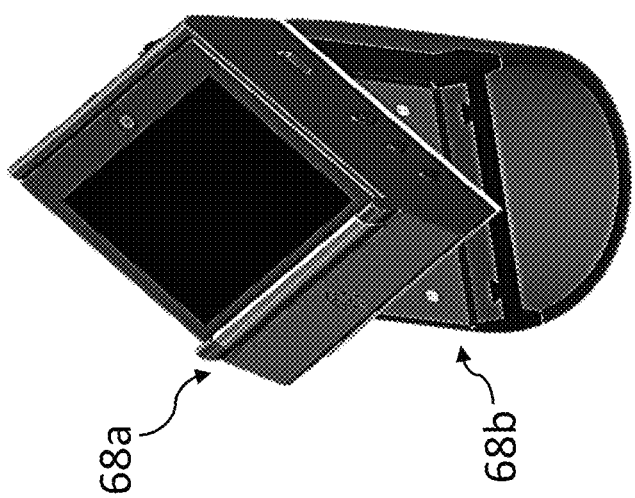
FIG. 12 illustrates another embodiment of the wearable care security smart watch device, wherein the screen is rotatable.

FIG. 12 illustrates the wearable care security smart watch device with a rotational function. The entire screen portion or main housing 68a of the wearable care security smart watch device may rotate from the strap portion 68b. The main housing 68a comprises the top half of the wearable care security smart watch device including the multiple screens, battery mechanisms, buttons, etc. The rotatable function allows the user to use the wearable care security smart watch device at multiple angles views. The differing views may be helpful for taking pictures, and different positions may achieve certain functions and view abilities. Herein, the rotatable feature has not been introduced to any watch phone device. The rotatable features also lets the user be creative and not be bound by the rules of wearing a smart watch phone device that only allows limited angle views.

Figure 13:
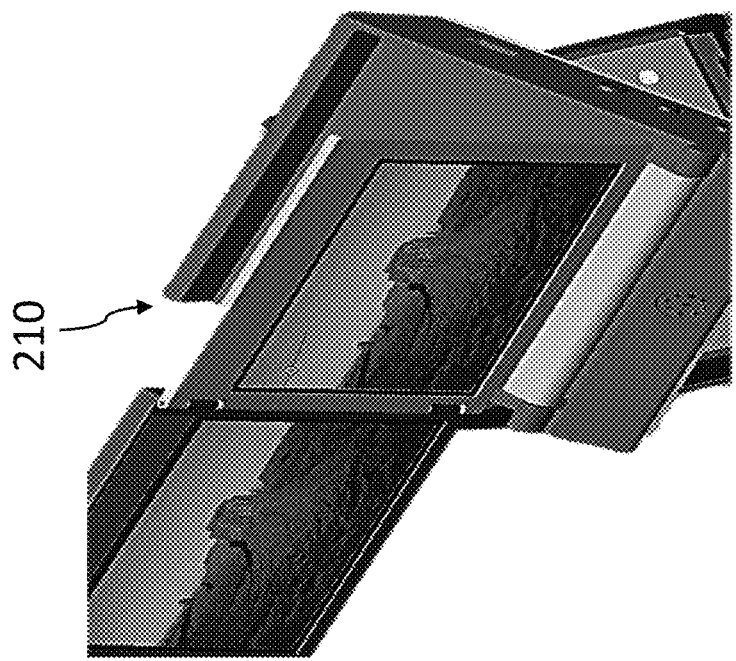
FIG. 13 illustrates yet another embodiment of wearable care security smart watch device, wherein the screen is angled at a 90 degree angle and still rotatable.

FIG. 13 illustrates the wearable care security smart watch device with the screen mechanisms in the 90 degree angle and also in rotation form 210. Herein, the wearable care security smart watch device may be adjusted to different angles and take pictures at the different angles. The feature will heighten the user experience. Further, because the wearable care security smart watch device may rotate and bend to different angles and positions, the wearable care security smart watch device is able to utilize a single camera instead of multiple cameras.

Figure 14:
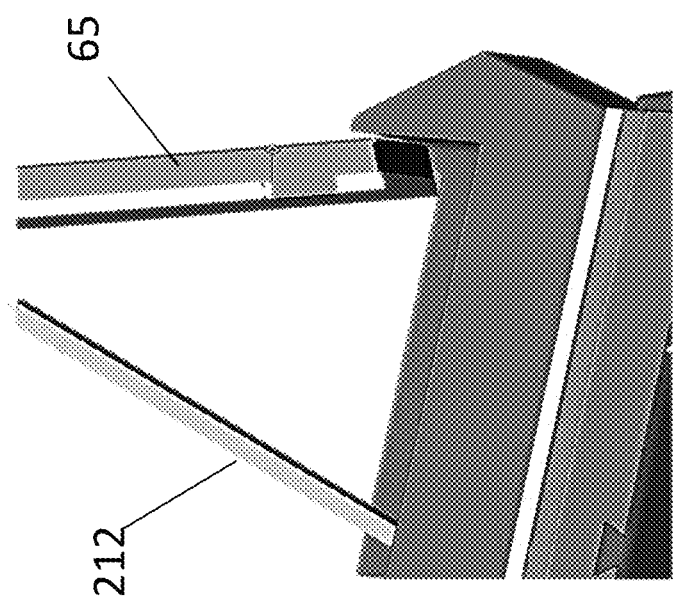
FIG. 14 illustrates one embodiment of the wearable care security smart watch device, wherein the stand mechanism of the wearable care security smart watch device is shown.

FIG. 14 illustrates one embodiment of a screen stand mechanism 212 that may be utilized to keep the screen mechanism in the upright position and will prevent the screen from falling which could result in damage. The stand mechanism 212 may hold the multiple screens 65a, 65b, 65c and will not interfere with the opening and closing of the overall wearable care security smart watch device.

Figure 15:
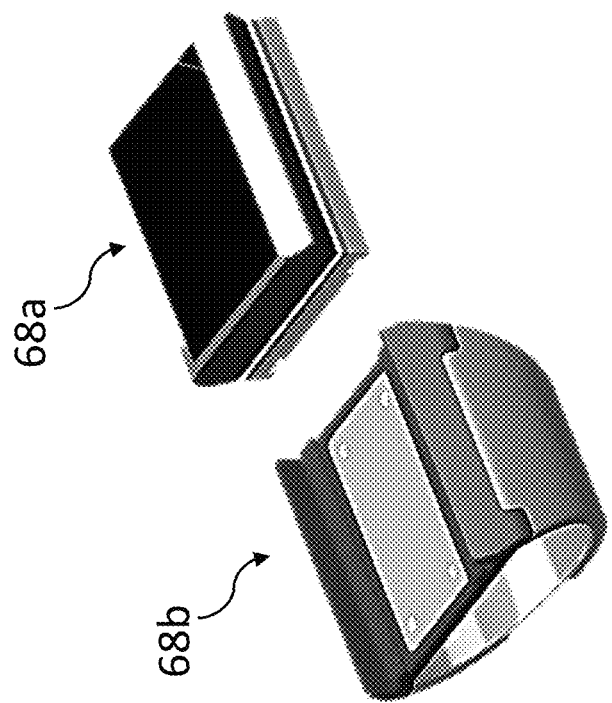
FIG. 15 illustrates another embodiment of the wearable care security smart watch device.

FIG. 15 displays yet another embodiment of the wearable care security smart watch device, wherein the main housing 68a has a removable function from the watch band 68b. This feature may allow the user preferences as to how he would want to use the device. For example, he may want to connect it to a stand for a table, wear it on a belt, clip it to multiple items such as a purse, motorcycle handle bar, etc. The device may be able to adapt to the needs of the user beyond a watch function on the user's wrist.

Figure 16:
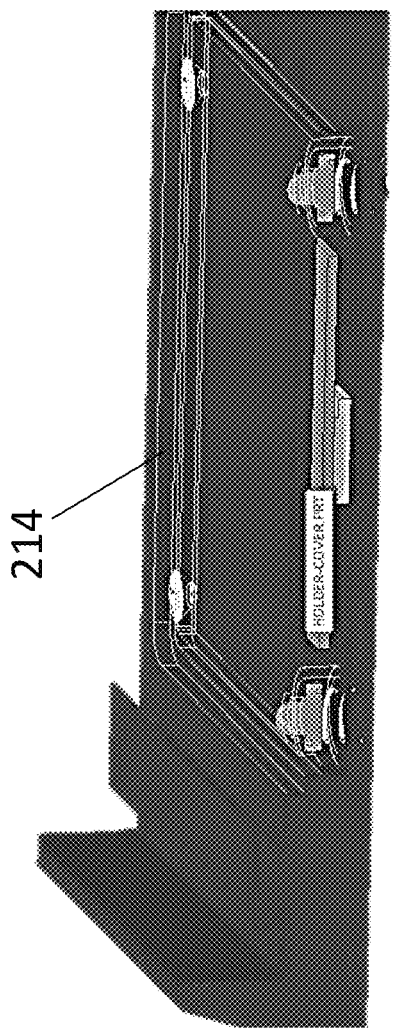
FIG. 16 illustrates another embodiment of the wearable care security smart watch device, specifically illustrating a heart rate monitor.

FIG. 16 illustrates an embodiment of a heart rate monitor PCB 214. The heart rate monitory may communicate with the main housing via Bluetooth. Thus, no wires will be present or within the housing which would interfere with the movement of the device. The heart rate monitor may run low energy-efficient and may not need a large battery to function but would be able to use a regular watch-like battery. Thus, the use of wires are eliminated and even when the wearable care security smart watch device's screen portion 68a is disconnected from the wrist, the device would still be able to communicate with the processor via Bluetooth and continue to record and store the user's heart rate readings.

Figure 17:
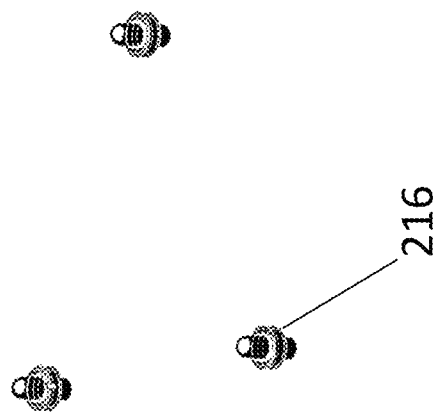
FIG. 17 illustrates an embodiment of push pins that may control the movement of the rotating base of the wearable care security smart watch device.

FIG. 17 illustrates an embodiment of a push pin mechanism 216. The push pin mechanisms 216 may control the movement of the rotating base of the watch device. The push pins may be spring loaded by having a spring installed into the housing and the push pin mechanism resting on top of a spring. In doing so, the push pin mechanisms will cause it to lock the rotating base in place and prevent movement.

Figure 18:
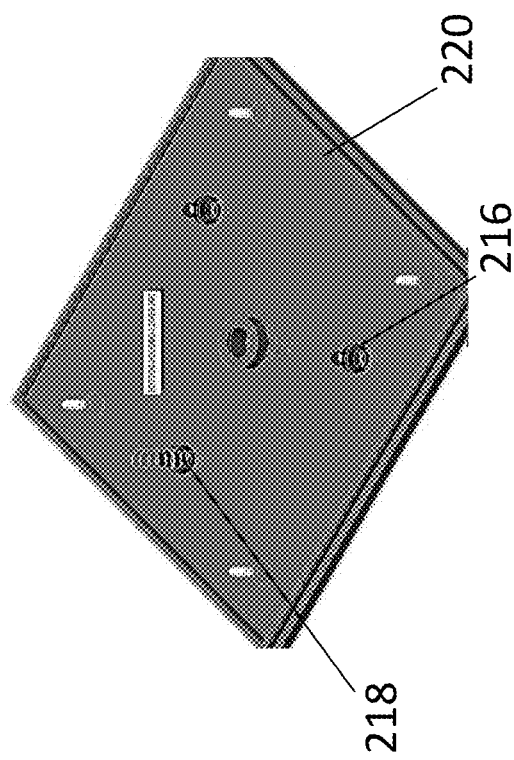
FIG. 18 illustrates an embodiment of a fixed plate that will house a push pin and a spring within the wearable care security smart watch device.

FIG. 18 illustrates the push pin mechanism 216 and a spring 218 on a fixed plate 220 that may house the push pins and springs.

Figure 19:
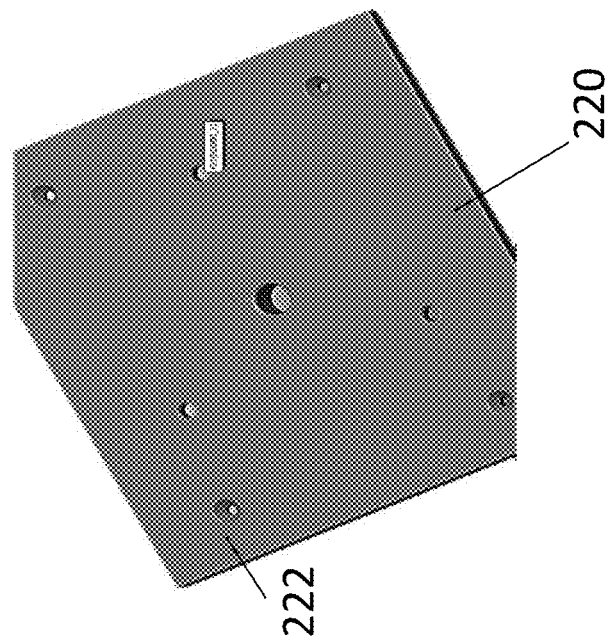
FIG. 19 illustrates the bottom angle of a main housing rotation base of the wearable care security smart watch device.

FIG. 19 illustrates the bottom view of the fixed plate 220. The apertures 222 are where the push pin mechanisms will stop the device at different moving positions. In design, the fixed plate will be able to achieve a full rotation of 360 degrees. As stated, no wires will need to travel through it.

FIG. 20 illustrates an embodiment illustrating how the push pin mechanisms 216 will help to hold the screen devices 68a from sliding out of the watch strap holder mechanism 68b. The screen device portion 68a will be able to move when the user applies a small amount of pressure.

A screw mechanism 224 will also help keep the rotation plate 220 and the main housing 68a together. In one embodiment, the screw mechanism 224 may be a small self-tap screw.

Figure 21B:
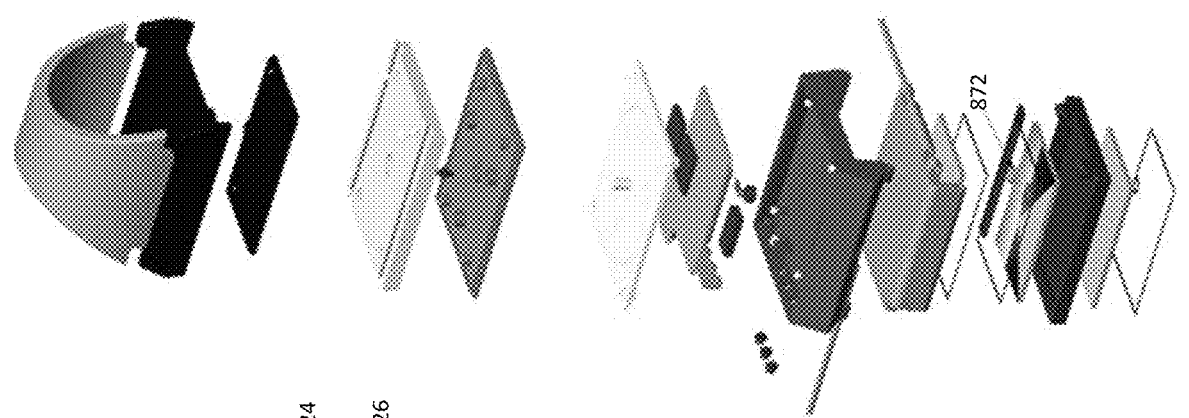
FIGS. 21*a* and 21*b* illustrate blown-up views of one embodiment of the wearable care security smart watch device and all its corresponding parts.
Figure 21A:
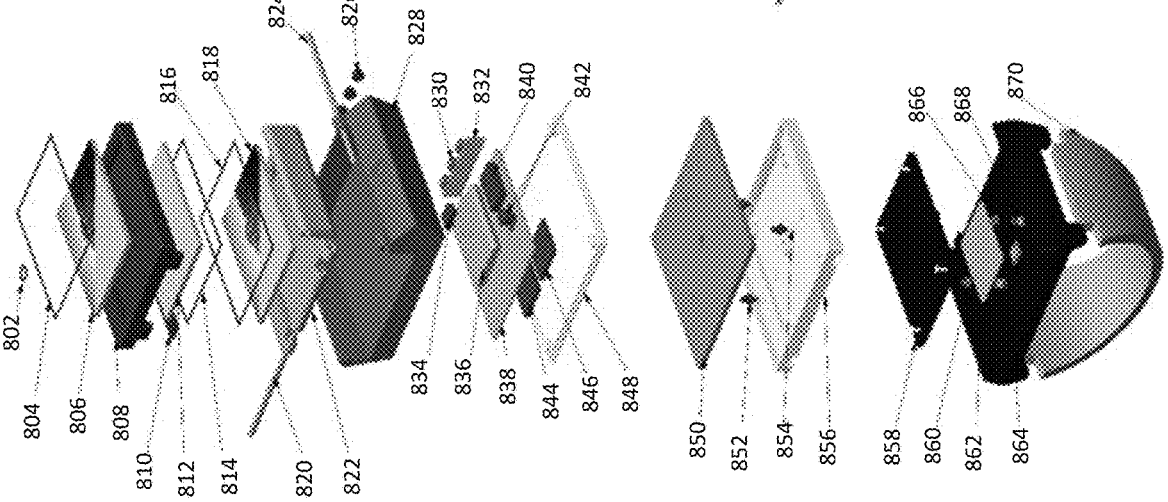

FIGS. 21a and 21b illustrate a blown-up view of one embodiment of the wearable care security smart watch device and all its corresponding parts. Herein, the blown-up view illustrates all the corresponding parts of the wearable care security smart watch device and how they may interact with each other. A camera lens 802 is located above a display lens 804 and a display 806 on top of a top display housing 808. A camera 872 aligns with the camera lens. A camera cover 810 is placed on top of a second display 812 and there may be a second display lens 814 and a third display lens 816 on top of a third display 818. A first hinge mechanism 820 attached through the bottom display housing 822 and a second hinge 824, along with at least three button mechanisms 826 attaches a main housing 828. A mechanical switch 830 may be connected to a switch PCB 832 and a Mic USB 834, as well as a battery mechanism 836 are all attached to a main PCB 838. A speaker mechanism 840 as well as a microphone mechanism 842 are also attached to the main PCB 838. A MIC SD card socket 844 and a MIC SIM card socket 846 are present and the main housing cover 848 complete the top portion of the wearable care security smart watch device.

The bottom portion of the wearable care security smart watch device comprises a rotation base top 850. The rotation base top 850 is attached to the rotation base bottom 856 with the use of the rotation pin mechanisms 852. Between the rotation base top and the rotation base bottom are also the rotation springs 854. A holder top 858 is attached to a holder bottom 864 with a holder stop pin 860 and holder stop spring 868. Within the holder top and holder bottom, there may be a heart rate monitor PCB 862. There is also the heart rate monitor 866. These are all attached a belt or strap 870 that may be adjustable and placed on the user's wrist.

In additional embodiments, the wearable care security smart watch device and system may be utilized to provide health care/security monitoring for the user. Additionally, the system may provide body security for persons who activate security functions. The system may provide private sector security and also provide police protection with GPS location triggers activated by heart rate functions.

Further, the wearable care security smart watch device and system may provide cell phone service globally. A user may also be able to create V.I.O.P. (video calls) network that will communicate with contacts on an additional phone line. While in use, a user may be able to eliminate minor doctor visits especially if they are unable to leave his residence, a doctor would be able to receive the user's health information and regulate and monitor any changes in the user's heart rate. Further, a user may be able to communicate with her doctor through Skype® and/or V.I.O.P. communications.

Like smart watches, the wearable care security smart watch device and system will be able to utilize mobile applications. For example, task planner evolution applications that will assist the user in tracking their calendar and agenda. It may be voice controlled and provide the user an easily accessible planner/scheduler. Further function may include the programmer setting up a planned agenda through the application and will be able to send it by inputting the user's phone number. The task planner would be a reminder tool to help the wearer keep track of their schedule, constantly remind wearer of agenda, common things forgotten throughout the day where they put their keys for example, or to remember medication schedules, pick up someone and would switch in between apps to accomplish different goals.

Another application that may be used by the wearable care security smart watch device and system includes a directional or programming application. This use would assist a user in accomplishing an unknown task like programing a television or assist in making scrambled eggs. The user would be able to activate the voice recognition system and the user will be able to search any question using the Internet. The application will search through the Internet and give the user the information relating to his question. The goal of an application like this would be to make the user more independent and prevent agitation which may interrupt the user's focus, productivity, and mood.

In an additional embodiment, a safe track program may be installed and programmed into the wearable care security smart watch device and system. This program will be able to navigate a wearer thru city by walking or driving to avoid high crime streets, areas, and subways integrating with current available servers and website hosts to use real time events or history of trouble areas.

Using this Data collected, the program would be able to find out what times of day crimes are more likely to occur and if or when the user should travel. It will keep the wearer up to date and if a crime is in progress will send message with voice prompt, divert wearer to another location. Similarly, if the user is driving in a car, the program will update as soon as there is a reported crime in progress or accident that the user should avoid.

The way the program would function is that if enabled, the program would bring up the wearers location using GPS satellite, working in conjunction with the local cities crime data website to guide the wearer through neighborhoods. The program would then act as a normal GPS turn by turn navigation system, directly the user to avoid certain areas, with the additional functions as a security measure to prevent going into crime filled neighborhoods.

The app would be able to detect current updates going on in the city and would redirect the wearer whether walking or driving to avoid troubled areas or areas of distress including fires, major catastrophes, and including heavy police crime scenes.

In an additional embodiment, the wearable care security smart watch device may be able to read and record the user's heart rate and save and record this data in order to analyze patterns. The program is designed so that if the user is having a medical condition or emergency and is unable to talk, a trigger of an emergency will be sent to emergency respondents that may decide to send an ambulance, police department, and/or fire fighters to the user's location via GPS location. Another example where security features would be important is if the user is being robbed or in a life threatening situation. The wearable care security smart watch device and system may use alerts and ask if the user is safe or okay. The user may be able to answer the question affirmatively and if no answer is made the wearable care security smart watch device and system will measure the user's heart rate and determine if it is above normal or in distress. If in distress, the wearable care security smart watch device and system may notify emergency respondents that you may be in distress. This program may be designed in multiple languages and be able to set up a key phrase or password that would be able to trigger a silent alarm. The program will then send the nearest emergency personnel to the user's location.

In further embodiment, the wearable care security smart watch device and system may have a medical aide service program. This program will allow users to make doctor appointments via video conferencing calls and will provide a visual of the user and doctor without leaving the comfort of the user's home or workplace. Through the program, a doctor would be able to analyze the user's vitals through the Internet via the heart rate monitor. The doctor may also be able to provide diagnoses of certain conditions to the user through Bluetooth wireless device accessories. This information would be stored into hardware memory or the preferred path of the USB port, which will be able to send data. If health conditions gets worse the doctor will be able to advise the wearer to seek medical help and save information on the hardware and or USB stick to be used to help doctors in hospital to know how to medically treat the user. This type of program would be able to help individuals in third world countries or foreign countries get medical help and attention from numerous countries and/or medical providers.

In these embodiments, of the of the services mentioned will be able to assist the user of the wearable care security smart watch device. These programs will be able to help assist and maintain users' regular schedules and life commitments. For the early stages, the device may be used as an assistant to a patient and also a caregiver. The device role is one of support and companionship. It is a device that will be there to help with the daily life of the user, as needed, and to help an individual with Alzheimer's and other dementia related illness function and plan for the future.

Thus, has been broadly outlined different uses of the wearable care security smart watch device. In no ways should the above be interpreted as the only functions of the wearable care security smart watch device. With practice, further embodiments may be developed that would further the use of the wearable care security smart watch device.

What is claimed is:

1. A wearable security device comprising:
   a strap;
   a watch face base attached to the strap;
   a first screen, in communication with the watch face base, wherein the first screen folds upwardly from the watch face base, forming a first screen panel that is perpendicular to the base;
   a second screen, wherein the second screen is located on a front side of a second screen panel;
   wherein the second screen panel is pivotably connected to the first screen panel; and
   wherein the second screen is in folding communication with the first screen;
   a third screen, wherein the third screen is located on a back side of the second screen panel;
   wherein the third screen is in communication with the second screen;
   wherein the second screen panel folds outwardly from the first screen panel; and
   wherein the second screen panel creats a two-sided panel display which can be tilted up or down according to viewing preference;
   a first heart rate monitor attached to a back side of the watch face base, wherein the heart rate monitor records at least one vital sign of a user;
   a memory; and
   at least one program, wherein at least one program is stored in the memory and configured to track the at least one vital sign of the user recorded by the heart rate monitor.

2. The wearable security device of claim 1, wherein the first, the second, and the third screens are 2-4 inch Thin Film Transistor ("TFT") touch screens.

3. The wearable security device of claim 1, wherein the watch face base is powered by lithium batteries.

4. The wearable security device of claim 1, where the watch face base further comprises a 2.0 mega pixel camera.

5. The wearable security device of claim 1 wherein the watch face further comprises a USB connection.

6. The wearable security device of claim 1, wherein the strap has sensitive touch dials.

7. The wearable security device of claim 1, wherein the watch face base comprises a rotational member wherein the rotational member comprises 180 degrees of rotation wherein the second and third screen angles can be adjusted vertically and horizontally to accommodate the user's preference.

8. The wearable security device of claim 1, wherein the watch face base comprises a pivotable mechanism configured to provide angular displacement flipability in order to provide different angles of viewing.

9. The wearable security device of claim 1 further comprising:
   a transmitter strap, wherein the transmitter strap further comprises:
      a waterproof band; and
      a second heart rate monitor attached to the waterproof band configured to read and send heart signals to the wearable security device.

10. The wearable security device of claim 1, wherein the first screen panel is attached to the watch face base by a first hinge, and the second screen and the third screen are attached to the first screen panel by a second hinge on an edge of the first screen panel.

* * * * *